United States Patent [19]
Scully et al.

[11] Patent Number: 5,198,222
[45] Date of Patent: Mar. 30, 1993

[54] TIME RELEASE BOLUS

[75] Inventors: Marlan O. Scully, Estancia; David Woodling, Albuquerque, both of N. Mex.

[73] Assignee: AgriBioTech, Inc., Las Vegas, Nev.

[21] Appl. No.: 575,583

[22] Filed: Aug. 31, 1990

[51] Int. Cl.$^5$ .............................................. A23K 1/18
[52] U.S. Cl. ................................. 424/438; 424/424; 424/452; 605/892.1
[58] Field of Search ............... 424/438, 452, 424; 604/892.1, 892.2

[56] References Cited

U.S. PATENT DOCUMENTS

| | | | |
|---|---|---|---|
| 3,797,492 | 3/1974 | Place | 128/260 |
| 3,844,285 | 10/1974 | Laby | 128/260 |
| 3,901,232 | 8/1975 | Michaels | 128/260 |
| 4,220,153 | 9/1980 | Dresback | 128/260 |
| 4,228,149 | 10/1980 | Brewer et al. | 424/14 |
| 4,251,506 | 2/1981 | Laby | 424/14 |
| 4,326,522 | 4/1982 | Guerrero et al. | 128/260 |
| 4,439,197 | 3/1984 | Honda | 604/891 |
| 4,564,363 | 1/1986 | Bagnall et al. | 604/891 |
| 4,623,345 | 11/1986 | Laby | 604/892 |
| 4,675,174 | 6/1987 | Eckenhoff | 424/15 |
| 4,687,480 | 8/1987 | Laby et al. | 604/891 |
| 4,976,966 | 12/1990 | Theeuwes | 424/473 |

Primary Examiner—Thurman K. Page
Assistant Examiner—D. Gabrielle Phelan
Attorney, Agent, or Firm—Ladas & Parry

[57] ABSTRACT

A time release bolus comprises a tubular member and an end cap secured to each other. The tubular member contains an inner bag which is adapted to receive and contain a nutrient or medicament substance. A capsule is provided in the tubular member, and upon fracture thereof, applies pressure to the inner bag. The end cap includes a plug which fits into an open end of the tubular member and a top portion. A passage is provided which leads from the tubular member to the exterior, such that nutrient or medicament can flow from the inside of the tubular member to the outside of the time release bolus. The bolus further includes in the end cap a mesh in the flow path of the substance, the mesh further restricting and controlling the amount of substance which may pass from the bolus to the exterior. Wings are provided on the end cap which are movable between a first retracted position where insertion per os of the bolus takes plus, and a second extended position adopted in the rumen to prevent regurgitation of the bolus.

14 Claims, 6 Drawing Sheets

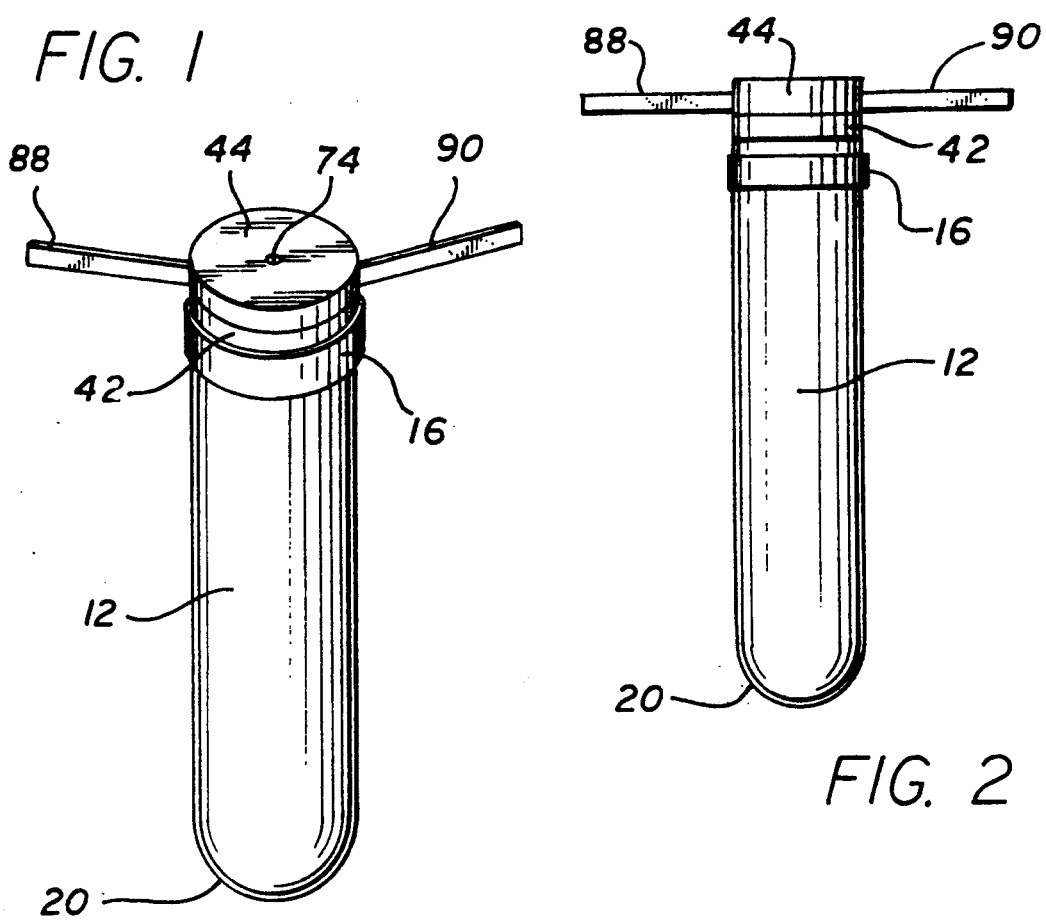
FIG. 1
FIG. 2
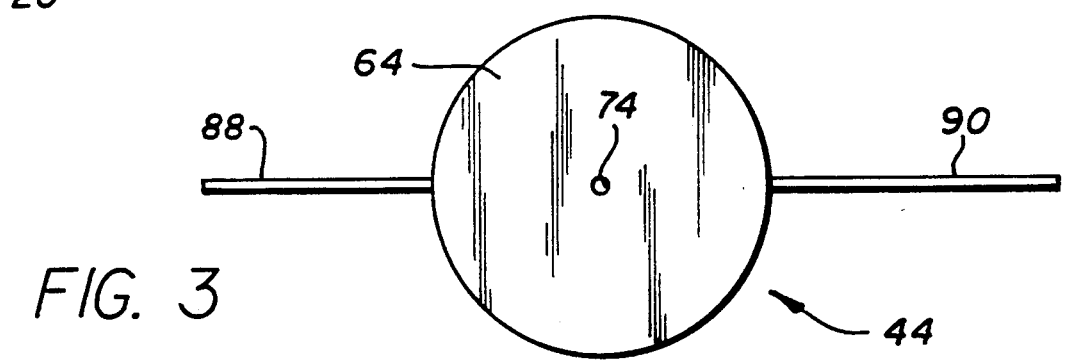
FIG. 3
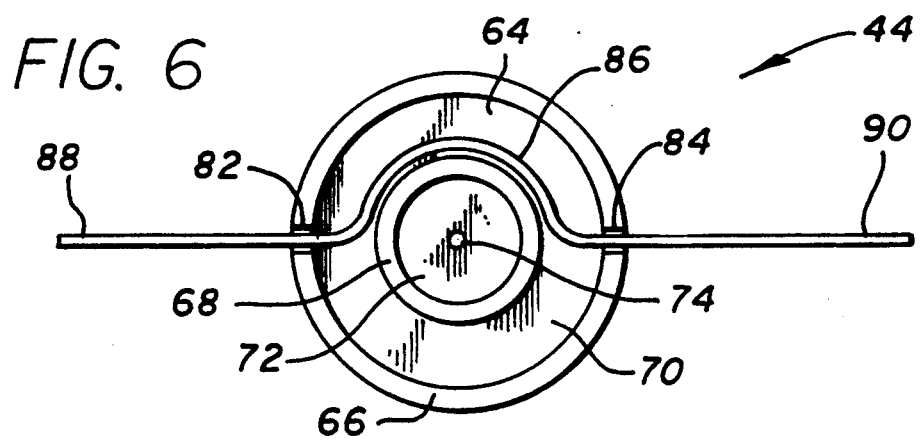
FIG. 6

TIME RELEASE BOLUS

FIELD AND BACKGROUND OF THE INVENTION

This invention relates to a time release bolus for administering a medicament or nutrient substance to a ruminant. The bolus is designed such that the contents thereof are released therefrom into the ruminant over an extended period of time. In this way, controlled amounts of nutrients and/or medicaments can be administered to the ruminant over a given time period so that daily or a very short term examination and treatment of the ruminant is substantially eliminated.

It is well known in the art to introduce into ruminants nutrients, medicaments, drugs or other dietary supplements by means of a system whereby the ruminant ingests a bolus which remains in, for example, the rumen thereof and dispenses its contents over a period of time. It is cumbersome and labor intensive to introduce into the daily food intake of such ruminants the required amount of any drug, medicament nutrient or other substance. A controlled time release bolus therefore has the significant advantage of providing the animal with nutrients and medicaments which will be released into the body over a period of time. In general, substances and nutrients beneficial to the animal can be included in all such time release boluses, while specific medicaments or substances required by a particular animal or group of animals in a given area may be included as well. In this way, any deficiencies in a particular area, or infectious agents peculiar to a specific location, can be included in the time release bolus, and the animal will receive appropriate supplements to dietary deficiencies, or medicaments or drugs which are able to counteract infections to which a particular animal, or a particular region, is susceptible.

A wide variety of devices for administering substances to ruminants are known in the prior art. For example, Laby (U.S. Pat. No. 3,844,285) discloses a device having a body portion containing the substance and adapted to assume a first configuration in which it can be administered per os to the animal, and thereafter changes into a second configuration to prevent or hinder regurgitation while in the rumen. Drespack (U.S. Pat. No. 4,220,153) teaches a delivery system for controlling release of chemicals using a device having a wall formed of a porous fabric material which is in contact with a reservoir containing the chemical. Brewer (U.S. Pat. No. 4,228,149) discloses a sustained release composition wherein a medicament is dispersed in a sheet of water insoluble polymer. The sheet may be constrained in a position which allows oral administration, namely, by rolling the sheet in a strip of paper which loses its adhesive properties once introduced into the rumen. The sheet unfolds, at the same time preventing or hindering regurgitation thereof.

Laby (U.S. Pat. No. 4,251,506) shows a controlled release device for administering active agents to ruminants comprising a tubular body adapted to receive a precast cylindrical plug of therapeutic composition. A plunger, in conjunction with a helical spring, biases the plug towards an opening of the tubular body. The opening is a restricted one, resilient projections controlling the exit of the precast cylindrical plug from the tubular member. The device further includes a pair of resilient arms extending away from the tubular body. The arms may, however, adopt a configuration whereby they abut the tubular member, and with this arrangement the device may be administered per os to the ruminant. Once in the rumen, the arms project outwardly at an angle to the tubular body thereby hindering or preventing regurgitation of the device.

Guerreio describes a bolus having a fine mesh completely encasing the medicament. A heavy metal core may be provided. Bagnall (U.S. Pat. No. 4,564,363) teaches a device for effecting delayed release of an active ingredient which is contained within a container, the device comprising a removable closure and an electrical control circuit for removal of the closure at a designated time to release the active ingredient. Laby, in U.S. Pat. No. 4,623,345, describes a capsule having two body portions of magnesium or an alloy thereof pivotally connected to each other for movement between a relatively small cross-sectional configuration in which the capsule can be administered per os into the rumen, and a relatively larger cross-sectional configuration which resists regurgitation. Laby, in U.S. Pat. No. 4,687,480, teaches a capsule comprised of a tubular body, a cap at one end and an access opening at the other. Wings are provided and are movable between a first position away from the tubular body and a second position against the tubular body. The shape and structure of the wings enable them to be applied closely the tubular body to permit easy introduction into the rumen. At the access open end, an annular disk is provided, and a plunger and coil spring bias tablets towards and out of the opening for introduction into the system of the ruminant.

SUMMARY OF THE INVENTION

According to one aspect of the invention, there is provided a bolus adapted to contain and release over an extended period of time a composition, the bolus comprising: a tubular member having a sidewall, a closed end and an open end, the tubular member being adapted to contain the composition; an end cap member sealingly fixed to the open end of the tubular member, the end cap member having a passage means therethrough to permit flow of the composition from the tubular member to outside of the bolus; pressure means inside the tubular member for pressuring the composition thereby urging the composition towards the passage means; and flow restraint means for controlling flow rate of composition from the end cap member.

Preferably, the bolus further comprises an inner containment member adapted to be located within the tubular member, the inner containment member being adapted to contain the composition. The inner containment member may comprise a flexible bag of generally tubular shape, the flexible bag having an open end, a sidewall and a closed end, the open end of the flexible bag being coaxial with and inside of the open end of the tubular member, wherein the tubular member and flexible bag are both sealingly connected to the end cap member.

Preferably, the end cap member comprises lower plug means attached to the tubular member and an upper closure member connected to the lower plug means. The lower plug means may comprise an outer cylindrical wall having ridges thereon, the outer cylindrical wall and ridges being adapted to secure with the open end of the tubular member. The lower plug means may further comprise a base wall, the outer cylindrical wall extending downwardly from the base wall, and a cylindrical projection extending upwardly from the base wall, the upper closure member having a corresponding cylindrical recess adapted to receive the cylindrical projection. The passage means may comprise a channel extending through the cylindrical projection and an orifice in the upper closure member which registers with the channel.

Conveniently, the flow restraint means comprises a filter mesh located between the channel of the cylindrical projection and the orifice in the upper closure member. The pressure means preferably comprises a gas contained in a capsule in the tubular member, the capsule in use being fractured to release the gas immediately prior to application of the bolus. Preferably, the upper closure member comprises an upper surface, a downwardly projecting outer cylindrical wall, a downwardly projecting inner cylindrical wall whereby an annular space is defined by the inner and outer cylindrical walls, the inner cylindrical wall defining the channel adapted to receive the cylindrical projection of the lower plug. A pair of diametrically opposed slots in the outer cylindrical wall may be provided with an elongate strip material preferably extending from one slot into the annular space and through the other slot, the elongate strip material extending radially outwardly from the slots to form a pair of wings.

BRIEF DESCRIPTION OF THE DRAWINGS

FIG. 1 is a perspective view of the time release bolus of the invention.

FIG. 2 is a front view of the bolus shown in FIG. 1.

FIG. 3 is a top view of the bolus shown in FIG. 1

FIG. 6 is an underview of a portion of the end cap showing mounting of the wings thereto.

DETAILED DESCRIPTION OF THE PREFERRED EMBODIMENTS

Figure 4:
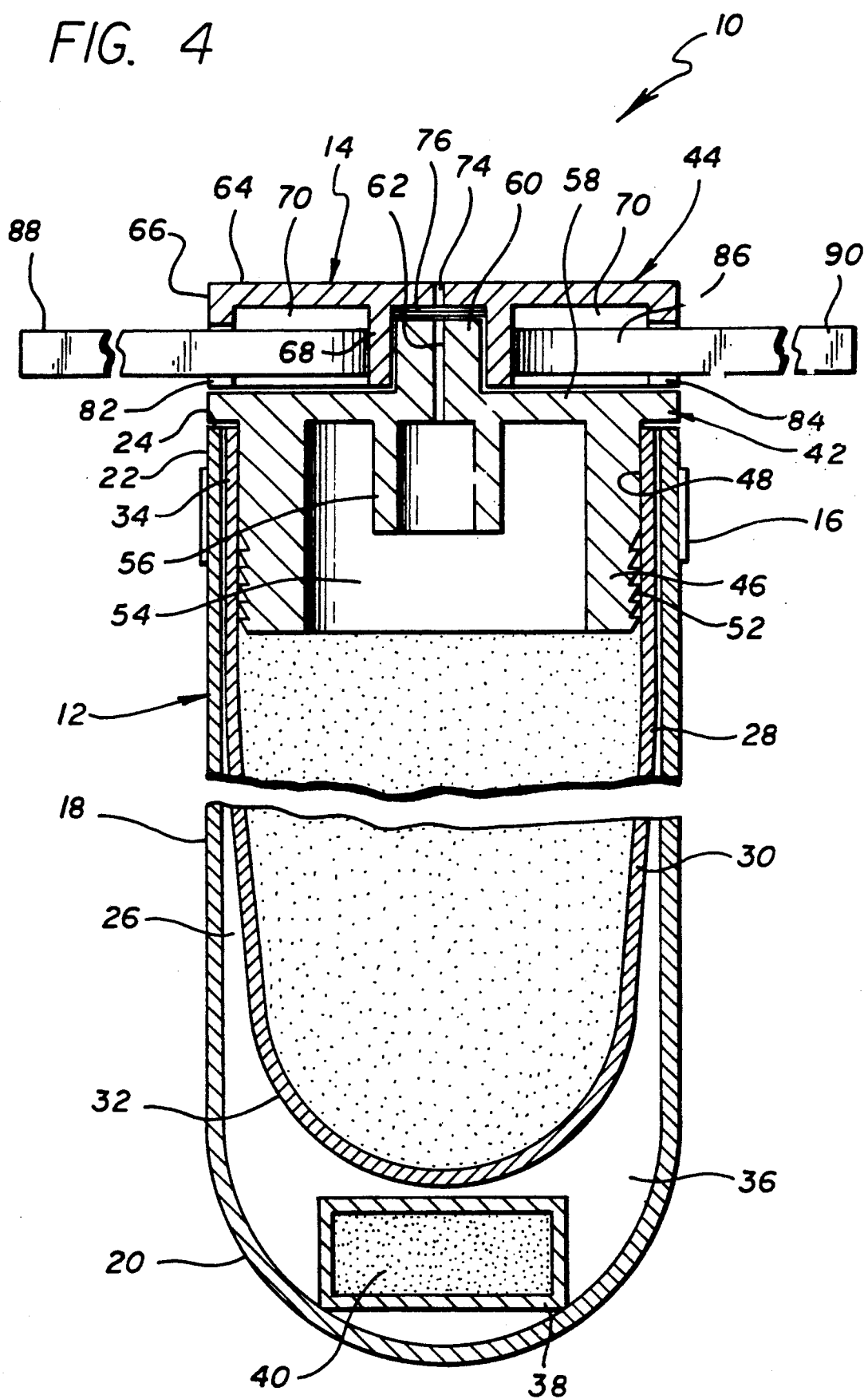
FIG. 4 is a cross section of the bolus.

Referring now to the figures, there is shown a time release bolus 10 comprising a plastic flexible tubular member 12 and an end cap 14. The end cap 14 and tubular member 12 are connected to each other to form a gas-tight seal, and the seal is strengthened by means of a press ring 16. The tubular member 12 is adapted to contain desired substances, such as nutrients, drugs, medicaments or other material, such substances being released over an extended period of time through the end cap 14. The time release bolus 10 is introduced into the rumen of a ruminant, and the tubular member 12 is of a size which is sufficient to contain nutrient or medicament substances to cater for the ruminants needs over a delayed period, such as thirty days, and the controlled time release of the substance into the ruminant insures that desired levels of the substances required are provided to the animal over the extended period. Due to the chosen structure of the microporous mesh used in the invention, as well as the properties of the nutrients and/or medicaments, a higher flow rate occurs for the first 7 to 14 days of the life of the bolus. This ensures proper rumen adjustment and aclimation. In a manner to be more fully described below, the rate of release of substances from the time release bolus may to a large extent be controlled by appropriate selection of materials, and adaptation of the physical and structural characteristics of the bolus 10.

The tubular member 12 comprises a side wall 18, a closed end 20, and an open end 22. The open end 22 of the tubular member 12 comprises a flat end edge 24. The side wall 18 and closed end 20 define a space 26, which is in use filled with a nutrient or medicament substance.

Located within the tubular member 12, there is provided an inner bag 28 having a side wall 30, a closed end 32, and an open end 34 which is of substantially the same or slightly smaller diameter than the open end 22 of the tubular member 12. The inner bag may be comprised of a plastic or latex composition. The side wall 30 of the inner bag 28 is shorter than the side wall 18 of the tubular member 12. Thus, when the inner bag 28 is mounted within the tubular member such that the open ends 22 and 34 of the tubular member 12 and inner bag 28 respectively are at the same level, a chamber 36 is provided between the closed end 32 of the inner bag and the closed end 20 of the tubular member 12. The chamber 36 contains a breakable plastic capsule or sealed plastic bag 38, the capsule or bag containing under pressure a fluorocarbon gas 40.

Figure 8:
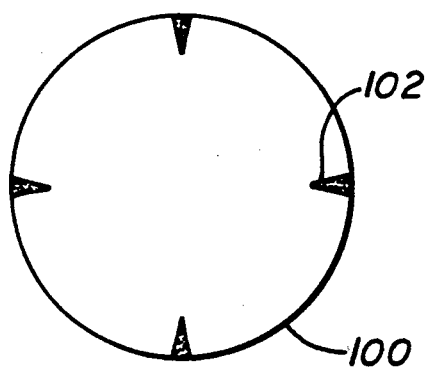
FIG. 8 is a diagrammatic view of a ring for use in conjunction with a capsule or bag for gas.
Figure 9:
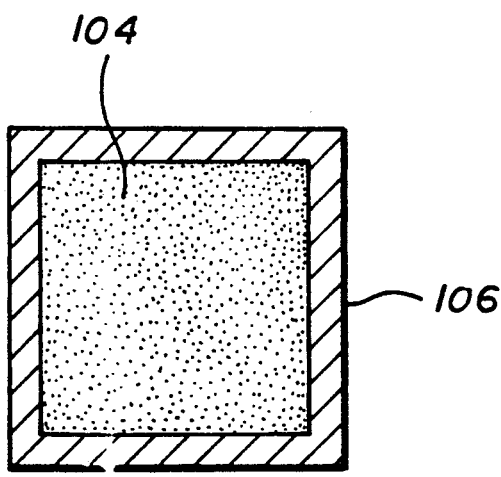
FIG. 9 is a top diagrammatic view of a capsule or bag for gas located in the bolus.
Figure 10:
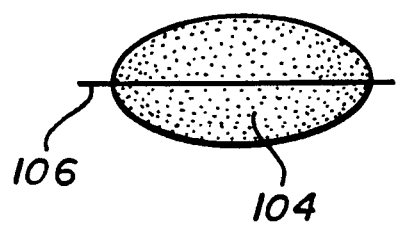
FIG. 10 is a side view of the capsule or bag shown in FIG. 9.

FIG. 8 shows a molded plastic ring 100 having a plurality of inwardly projecting points 102. In FIG. 9, there is shown a sealed bag 104, sealed at its edges 106, for containing the fluorocarbon gas. The sealed gas bag is located, in use, within the ring 100, and both are placed in the chamber 36. The ring 100 is sufficiently rigid to remain concentric under normal packaging and transportation conditions. However, once a force is applied to the ring 100 by squeezing it, typically between the thumb and forefinger, the inwardly projecting points 102 pierce the capsule or bag 104 thereby releasing the fluorocarbon gas into the chamber 36.

Figure 5A:
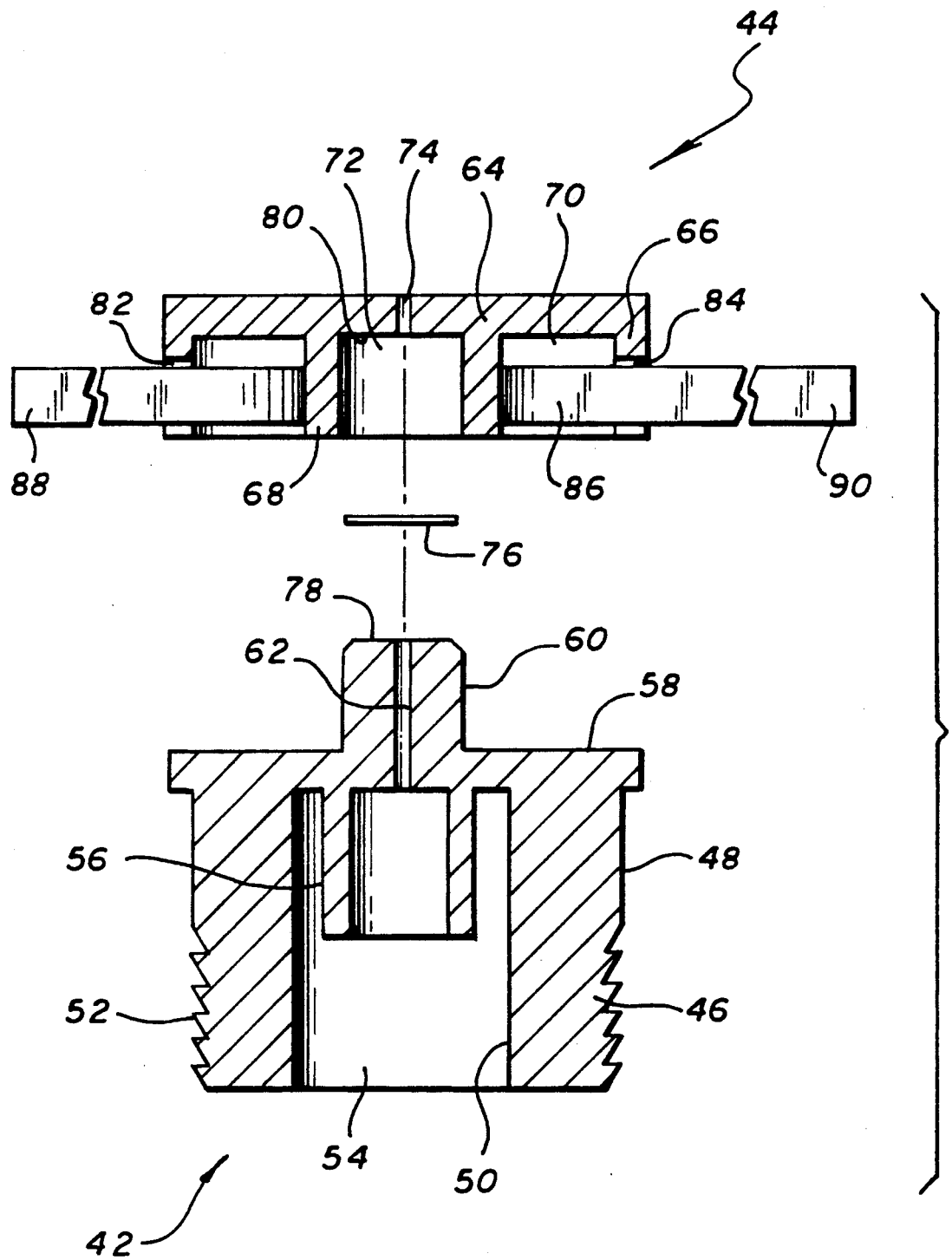
FIG. 5A is an exploded cross section of the end cap of the bolus.

Reference is now made to FIG. 5A of the drawings which shows an exploded cross-section of the end cap 14 of the time release bolus 10. The end cap 14 comprises a lower plug 42, which sealingly engages with tubular member 12 and inner bag 28 as described below, and an upper closure 44.

The plug 42 comprises an outer cylindrical wall 46. The cylindrical wall 46 has an outer surface 48 and an inner surface 50, the outer surface 48 having a series of ridges 52 to facilitate engagement with the tubular member 12. The cylindrical wall 46 defines a space 54 which contains an inner cylindrical wall 56. The plug 42 further comprises a base wall 58 and extending therefrom a cylindrical projection 60. The cylindrical projection 60 defines a passage 62 which extends from the space 54 to the outside of the plug 42.

The upper closure member 44 comprises a flat top portion 64, an outer downwardly extending sidewall 66 and an inner downwardly extending sidewall 68. Sidewalls 66 and 68 define therebetween an annular space 70, while inner sidewall 68 defines a cylindrical channel 72. An orifice 74 extends from the cylindrical channel 72 through the flat top portion 64 to the exterior.

A microporous mesh 76 having a diameter substantially the same as the cylindrical channel 72 is provided. In use, the plug 42 is mounted with respect to the upper closure member 44 by inserting the cylindrical projection 60 into the cylindrical channel 72. The cylindrical projection 60 fits tightly within the cylindrical channel 72 so that separation of the upper closure member 44 from the plug 42 requires a considerable force. When the cylindrical projection 60 is mounted within the cylindrical channel 72, the passage 62 and the orifice 74 are in registration. Thus, any substances flowing from the tubular member 12 into the space 54 pass through the passage 62 and to the exterior via the orifice 74. The mesh 76 is located between the upper surface 78 of the cylindrical projection 60 and the lower surface 80 of the flat top portion 64 so that substances flowing from the tubular member 12 to the exterior through the orifice 74 must pass through the mesh 76, which has the effect of keeping rumen foodstuff from the flow passage and/or filtering and controlling the amount of substance which may be expelled from the tubular member 12. The mesh 76 may be selected so that the porosity thereof controls outflow of substances according to predetermined need. As needs or substances introduced into the rumen in the time release bolus are varied or changed, mesh 76 may be changed accordingly to meet the requirements of extended release of substances into the rumen.

Figure 5B:
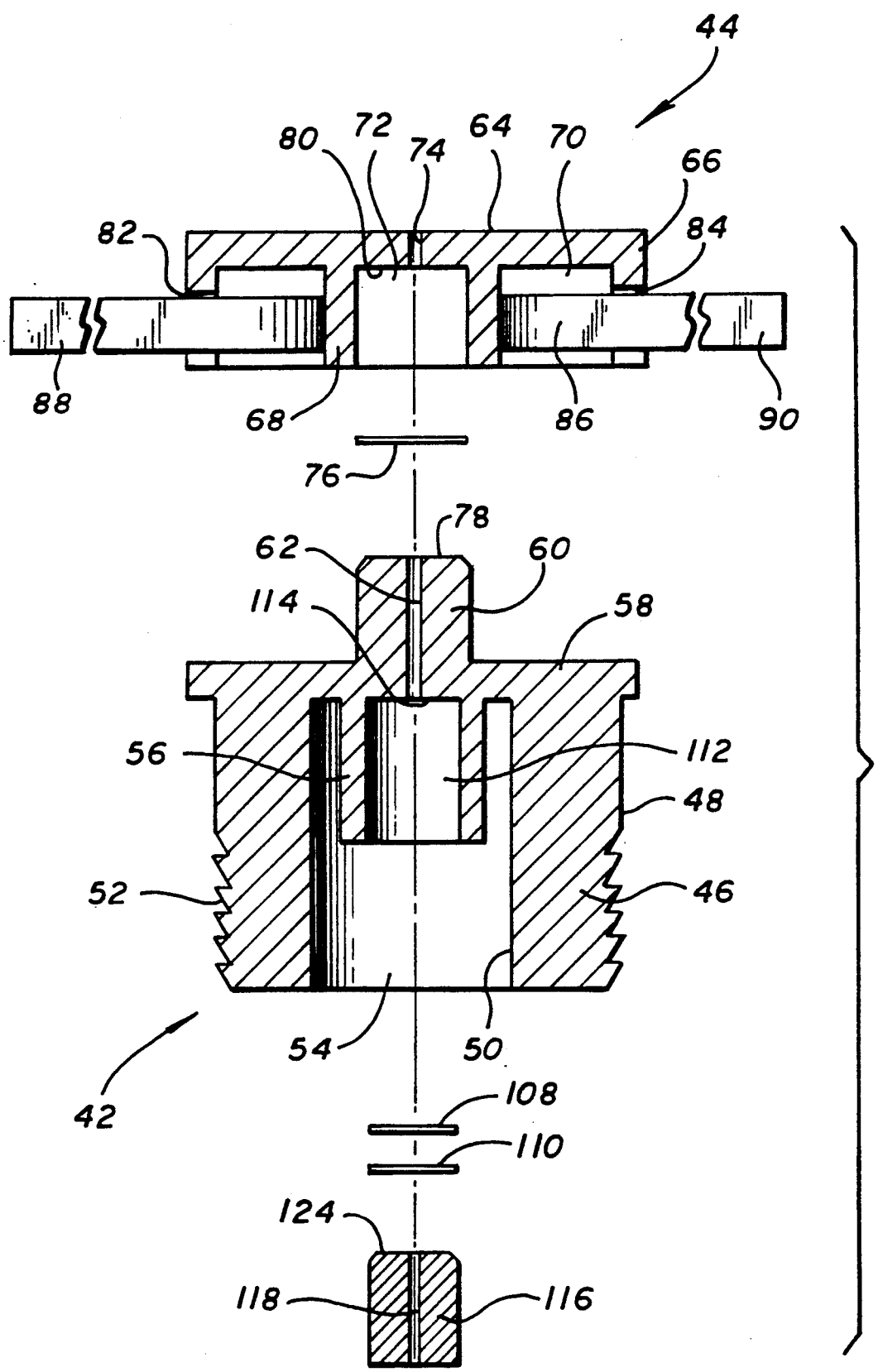
FIG. 5B is an exploded cross section of the end cap of a second embodiment of the bolus.

With reference to FIG. 5B, there is shown a second embodiment of the end cap 14. In most respects, the end cap comprising the plug 42 and upper closure 44 is in all material respects identical to that described with reference to FIG. 5A, and the same reference numerals are used in FIG. 5B. In the embodiment shown in FIG. 5B, there is further provided an upper seal mesh 108 and a lower seal mesh 110. The upper and lower seal meshes 108 and 110 are in use located in the chamber 112 defined by cylindrical wall 56. The chamber 112 is defined by the wall 56 and upper surface 114. The upper and lower meshes 108 and 110 are, in use, located against this upper surface 114. A seal plug 116, having a diameter slightly larger than the diameter of the chamber 112 (preferably larger by approximately 0.010 inches) is received within the chamber 112. The seal plug 116 includes a passage 118 to permit fluid flow from inside the bolus to the exterior.

Figure 5C:
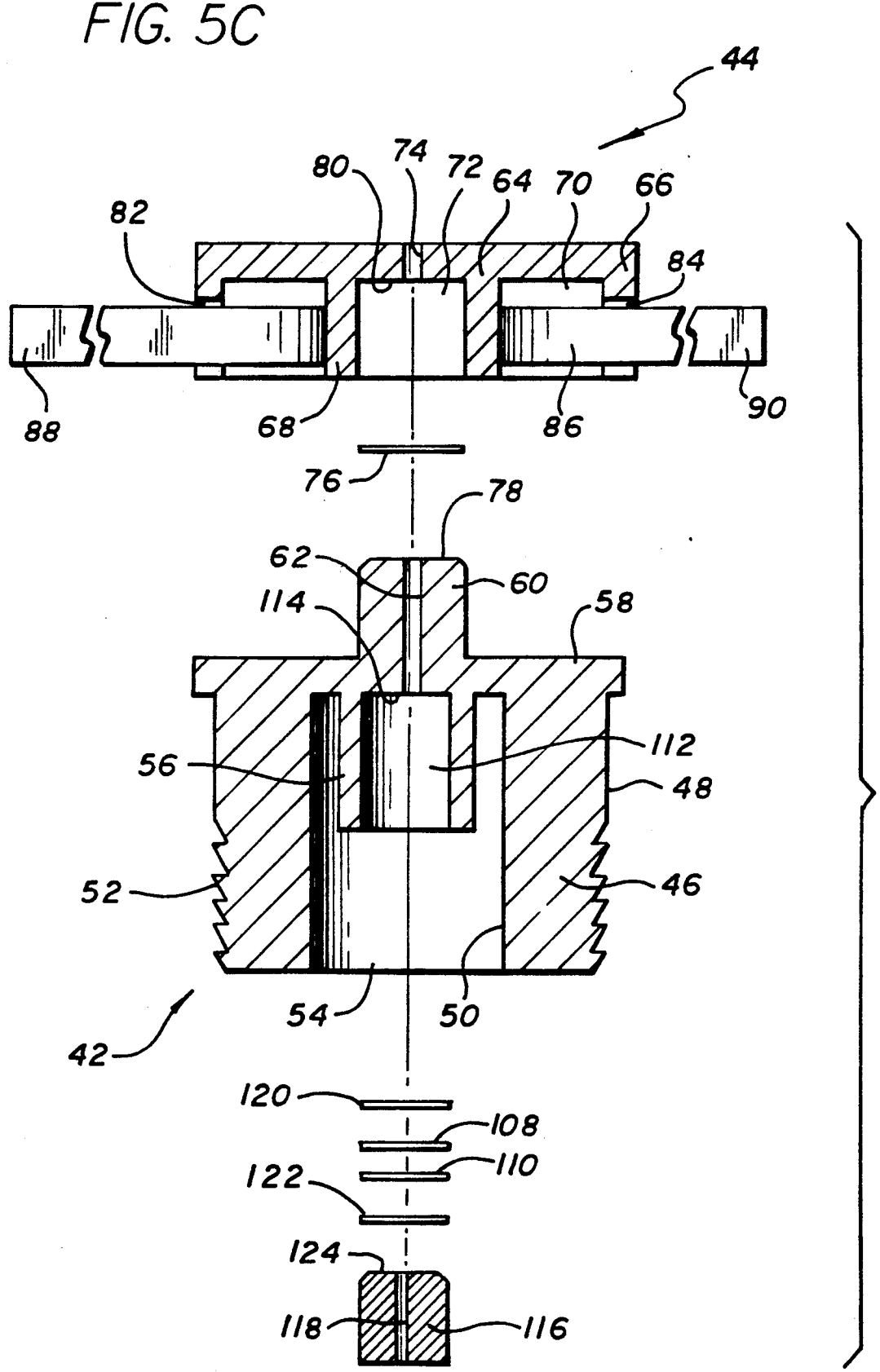
FIG. 5C is an exploded cross section of the end cap of a third embodiment of the bolus.

With reference to FIG. 5C of the drawings, an embodiment very similar to that shown in 5B is provided, except that an upper O-ring 120 and a lower O-ring 122 are provided. The O-rings 120 and 122 are located on each side of the upper and lower seal meshes 108 and 110 respectively and sandwich the upper and lower meshes therebetween inside the chamber. As described with reference to FIG. 5B, the seal plug 116, having passage 118, is forced into the chamber 112 and holds the O-rings 120 and 122, and the seal meshes 108 and 110 sandwiched therebetween, in position. The O-rings may be cut from a latex material.

In the embodiments described in FIGS. 5B and 5C, the seal meshes 108 and 110 have meshes of approximately 5.0 microns. The passage 118 in the seal plug 116 can be varied in diameter to increase or decrease flow rate of fluid from the bolus, as described. In FIG. 5C, the O-rings facilitate the seal of the seal meshes between the upper surface 124 of the seal plug, and the surface 114.

It will thus be appreciated that there are two different mesh locations. A first mesh 76 is provided between upper surface 78 of the plug 42 and lower surface 80 of the flat top portion 64. Such a mesh is typically for filtering and preventing foodstuffs in the rumen from entering the bolus. The second flow meshes 108 and 110 are located in the chamber 112, between the surface 114 and the seal plug 116. Typically, such meshes are used to set and control the flow rate of fluid from the bolus.

The outer sidewall 66 has a pair of diametrically opposed slots 82 and 84. A flat elongate strip 86 of plastic material extends through a first slot 82 into the annular space 70 around the inner sidewall 68 and through the slot 84. Outside of the flat top portion 64, the strip 86 forms a pair of wings 88 and 90. In the normal condition, the wings 88 and 90 extend outwardly in an essentially radial position, although the strip 86 is comprised of a flexible material so that the wings 88 and 90 can be bent to a position which essentially follows the periphery of the outer sidewall 66. Further details relating thereto will be discussed below.

In operation, an inner bag 28, which is comprised of a non-permeable gas-tight material, is filled at its open end 34 with substances such as drugs, medicaments and/or nutrients as required in the circumstances. A molded plastic ring 100 is inserted in the chamber 36. A plastic capsule 38 is dropped in at the open end 22 of the tubular member 12 and falls to the bottom so as to be located in the ring 100 and rest in the chamber 36 and on the closed end 20. Thereafter, the inner bag 28, containing the substance composition, is inserted into the open end 22 of the tubular member until the open end 34 of the inner bag 28 and open end 22 of the tubular member are at the same level. At this point, the inner bag 28 will fill most of the space defined by the tubular member 12, and the plastic capsule 38 will be located in the chamber 36 between the closed end 32 of the inner bag 28 and the closed end 20 of the tubular member 12.

With the open ends 22 and 34 of the inner bag 28 and tubular member 12 respectively at the same level, the open ends 22 and 34 are moved over the ridges 52 of the lower plug 42. The diameter of the inner bag 28 and tubular member 12, at their open ends, are the same or slightly smaller than the diameter of the outer surface 48 of the plug 42, and are stretchably forced thereover so as to form a very tight seal. The ridges 52 are designed to facilitate sliding of the tubular member 12 and inner bag 28 over the outer cylindrical wall 46 towards the base wall 58, but make it difficult to pull the inner bag and tubular member off the plug. The relatively sharp edges defined by the ridges are biased to engage the surface of the inner bag 28 and tubular member 12 when moved in one direction, namely, off the outer surface 48, but not in the other direction, namely, when moved towards the base wall 58.

In order to provide the connection between the lower plug 42 on the one hand, and the tubular member 12 and inner bag 28 on the other, a press ring 16 is mounted on the outer surface of the tubular member 12 so as to securely sandwich the tubular member and inner bag between the press ring 16 and the outer surface 48 of the outer cylindrical wall 46.

Before the lower plug 42 and tubular member 12 are firmly connected to each other, the upper closure member 44 is forced over the cylindrical projection 60, the cylindrical projection 60 being received in the cylindrical channel 72, as described above. Furthermore, the mesh 76 is located between the upper surface 78 of the cylindrical projection 60 and the lower surface 80 of the flat top portion 64. The flat elongate strip 86 is inserted in the flat top portion 64 in a manner already described, and since the cylindrical projection 60 is of slightly larger diameter than the cylindrical channel 72 (preferably 0.010" larger), a very tight fit is formed and the upper closure member 44 and lower plug 42 are firmly secured to each other. To facilitate the join between these two parts, glue or other adhesive may be used to insure that they do not come apart.

Figure 7:
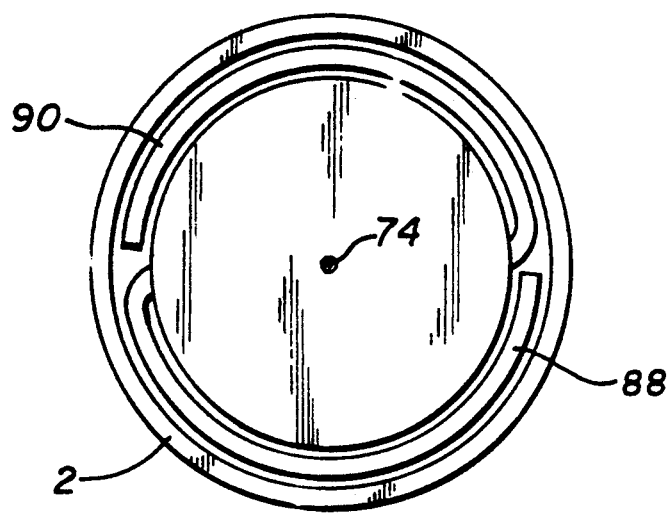
FIG. 7 is a top view of the bolus with the wings in the folded position.

The time release bolus is now fully loaded and ready for use, and, prior to insertion into the rumen, the wings are wrapped concentrically around the outer sidewall 66 to effectively reduce the diameter of the end cap 14. The wings are held in that position around the outer sidewall by means of a ring 92 which dissolves in the rumen after a short period, as best shown in FIG. 7. Instead of a ring, tape, wax or other suitable means may be used.

Immediately prior to insertion of the bolus per os, the closed end 20 of the tubular 12 is squeezed, which causes rupturing of the plastic capsule 38. Rupturing of the capsule results in the concomitant release of pressurized gases therein, and the gases occupy the space between closed end 32 of the inner bag 28 and the closed end 20 of the tubular member 12. The released gases exert pressure on the closed end 32 of the inner bag, and have the effect of placing the contents of the inner bag under pressure such that the contents will be urged towards and out of the passage 62 and orifice 74.

The time release bolus 10 is thereafter introduced into the rumen per os. The wings, being wrapped around the upper closure member 44, do not provide any significant obstruction, and the bolus 10 passes to the rumen of the animal. In the rumen, the ring restraining and holding the wings wrapped around the upper closure member 44 is dissolved, and the resilience of the wings causes them to unroll and extend radially outwardly from the upper closure member. Effectively, unwrapping of the wings substantially increases the diameter of the end cap 14, and hinders and obstructs regurgitation of the bolus 10 from the rumen. In this way, the bolus 10 is securely lodged in the rumen and will expel the substances contained therein over a given period.

Depending upon the size of the passage 62 and orifice 74, as well as the porosity of the mesh 76, the rate of flow of the substance from the inner bag 28 can be varied. Faster flow can obviously be achieved by increasing the diameter of passage 62 and orifice 74, and/or providing a mesh of increased porosity. The converse would also apply. In addition, the rate of flow of the composition from the end cap 14 can to some extent be controlled by the nature and extent of the gas contained in the plastic capsule. Thus, upon rupturing of the capsule, according to the nature and amount of gas used, a different degree of pressure will be exerted on the inner bag 28 resulting in an increased or reduced flow rate from the end cap 14.

It will thus be appreciated that, by the capacity to vary certain structural configurations and pressures of the time release bolus, a very accurate and precise rate of outflow can be achieved, taking into account the substance contained therein, the viscosity of the composition, the intended effect and daily requirements of the ruminant for a particular substance, and such other factors may be pertinent. The flow rate can be adjusted by varying any one or more of the following:
a. size of the passage 62
b. appropriate selection of meshes 108 and 110
c. appropriate selection of nature and quantity of gas to be contained in the plastic capsule.
d. appropriate selection of diameter of seal plug (116) passage 118.

One of the advantages of the breakable capsule 38 described above is that the internal pressure in the tubular member 12 can be initiated and created at the desired time. Heretofore, internal pressure may have been created after a certain temperature had been exceeded, which temperatures were normally encountered in the rumen. The present invention is not temperature dependant for activation, and thus has definite storage and transport advantages. The internal pressure with the breakable plastic capsule as described above will not be created, irrespective of any normal temperature fluctuations through which the time release bolus moves in storage or transportation, and can be simply and effectively activated by simply squeezing the closed end 20 of the tubular member 12 at the appropriate time. Under normal circumstances, the strength of the wall of the tubular member 12 would be sufficient to protect the capsule from being squashed or fractured unless a considerable force was applied, and the release of the pressure in transport or storage would therefore not be a significant problem.

The wings are comprised of a plastic flexible material which, as described above, unwrap upon dissolution of an adhesive wrapping them about the end cap after insertion per os. The wings are constructed of a plastic material which fatigues after a given time, the given time exceeding the material flow cycle from the tubular member 12. Upon fatigue, the wings break off from the end cap and will allow regurgitation of the bolus. In this way, the bolus, upon completion thereof, is regurgitated and expelled from the body.

It is to be noted that the porous mesh 76 has a dual function. Not only does it permit flow rate of substances or compositions contained in the inner bag 28 to be regulated, but it also prevents foodstuffs contained in the rumen from entering the bolus. Furthermore, the gas obviates the need for any plungers, springs or other complicated material in the tubular member 12 which may fail in use, and the use of the plastic capsule allows the bolus to be immediately effective in the rumen, since no heating up period or cooling down period of any gas which is temperature sensitive therein is required. The pressure is placed upon the active composition and substance as soon as the plastic capsule is broken, which occurs immediately prior to insertion per os.

Properties and effects of two fluorocarbons are discussed below in the following examples.

Properties

FC-72

Density = 1.68 gm/ml
Boiling Range = 56° C.
MW = 340 gm/mol
$P_{72}$ = Vapor pressure at 100° F. (38°) = 420 Torr

FC-87

Density = 1.62 gm/ml at 25° C.
Boiling range = 28°–38° C.
MW = 295 g/mol
$P_{87}$ = Vapor pressure at 100° F. (38° C.) = 1100 Torr

EXAMPLE 1

Calculate vapor pressure of 30% FC-72, 70% FC-87 @ 100° F.

$$X_{72}P_{72}+(1-X_{72})=P_{TOT}$$

Where
$X_{72}$ = mole fraction of FC-72
$P_{72}$ = Vapor pressure of FC-72
$P_{87}$ = Vapor pressure of FC-87
% wt FC-72 = 30.8%

$$\% \text{ wt } FC\text{-}72 = \frac{340X_1}{340X_1 + 295X_2} \times 100$$

$X_1 = 0.278$
$P_{TOT} = 0.278 \ (420\text{TORR}) + (1-0.278)1100\text{Tor} = 911$ Torr
911 Torr = 1.198 Atm = 17.62 psi absolute
Pressure in Albuquerque = 11.6 psi
$P_{bolus\ gage} = 6$ psi

EXAMPLE 2

For 80% FC-87, 20% FC-72 mix $$\% \text{ wt } FC\text{-}72 = \frac{20(1.68)}{20(1.68) + 80(1.62)} = 20.6\%$$

$$\% \text{ wt } FC\text{-}72 = \frac{34X_1}{340X_1 + 295(1-X_1)} \times 100$$

$X_1 = 0.184$
$P_{TOT} = (0.184) \ (420 \ \text{TORR}) + (1-0.184)(1100\text{TORR}) = 974\text{TORR}$
974 Torr = 1.282 Atm = 18.84 psi absolute
In Albuquerque: $P_{bolus\ gage} = 7.25$ psi The invention is not limited to the precise constructional details herein before described or illustrated. For example, any suitable end cap having a controlled outlet orifice, and/or limiting insertion of the mesh 76, may be used. Further, the wings may be attached to the end cap or other portion of the bolus 10 using any suitable means.

We claim:

1. A bolus adapted to contain and release over an extended period of time a composition, the bolus comprising:
   a tubular member having a side wall, a closed end, and an open end;
   an inner containment member adapted to be located within the tubular member, the inner containment member adapted to contain the composition;
   an end cap member sealingly fixed to the open end of the tubular member, the end cap member having an outer wall and a passage means therethrough to permit a flow of the composition from the tubular member to the outside of the bolus, the end cap member further comprising ridges on the outer water to facilitate fixing of the end cap member to the tubular member;
   pressure means inside the tubular member and outside the inner containment member for pressure the composition thereby urging the composition towards the passage means;
   flow restraint means for controlling flow rate of composition from the end cap member, the flow restraint means including a flow mesh located in the end cap in a path of the passage means;
   radial arms on the end cap member.

2. A bolus as claimed in claim 1 wherein the inner containment member comprises a flexible bag of generally tubular shape, the flexible bag having an open end, a sidewall and a closed end, the open end of the flexible bag being coaxial with and inside of the open end of the tubular member, wherein the tubular member and flexible bag are both sealingly connected to the end cap member.

3. A bolus as claimed in claim 2 wherein the pressure means is located in a space defined between the flexible bag and the tubular member.

4. A bolus as claimed in claim 1 further comprising a press ring for securely mounting the tubular member to the end cap member.

5. A bolus as claimed in claim 1 wherein the end cap member comprises lower plug means attached to the tubular member and an upper closure member connected to the lower plug means.

6. A bolus as claimed in claim 5 wherein the lower plug means comprises an outer cylindrical wall having the ridges thereon, the outer cylindrical wall and ridges being adapted to secure with the open end of the tubular member.

7. A bolus as claimed in claim 6 wherein the lower plug means further comprises a base wall, the outer cylindrical wall extending downwardly from the base wall, the lower plug means further comprising a cylindrical projection extending upwardly from the base wall, the upper closure member having a corresponding cylindrical recess adapted to receive the cylindrical projection, the passage means comprising a channel extending through the cylindrical projection and an orifice in the upper closure member which registers with the channel.

8. A bolus as claimed in claim 7 wherein the flow restraint means is a partial flow restraint means and comprises a filter mesh located between the channel of the cylindrical projection and the orifice in the upper closure member.

9. A bolus as claimed in claim 1 wherein the pressure means comprises a gas contained in a capsule in the tubular member, the capsule in use being fractured to release the gas immediately prior to application of the bolus.

10. A bolus as claimed in claim 9 wherein the gas comprises a fluorocarbon gas.

11. A bolus as claimed in claim 1 wherein the radial arms extend outwardly from the end cap, the radial arms being movable between a first position wherein the arms are wrapped about the end cap member, and a second position wherein the arms extend radially outward from the end cap member, the bolus being applied by mouth when the arms are in the first position, the arms in use moving to the second position inside a rumen.

12. A bolus as claimed in claim 11 wherein the radial arms are held within the withdrawn position by adhesive means, the adhesive means being dissolvable after a relatively short period after introduction thereof to the rumen.

13. A bolus as claimed in claim 11 wherein the radial arms comprise a material which will fatigue after a period of time and break off, thereby permitting in use regurgitation of the bolus.

14. A bolus as claimed in claim 8 wherein the upper closure member comprises: an upper surface; a downwardly projecting outer cylindrical wall; a downwardly projecting inner cylindrical wall whereby an annular space is defined by the inner and outer cylindrical walls, the inner cylindrical wall defining the channel adapted to receive the cylindrical projection of the lower plug;, and a pair of diametrically opposed slots in the outer cylindrical wall, an elongate strip material extending from one slot into the annular space and through the other slot, the elongate strip material extending radially outwardly from the slots to form a pair of wings.

* * * * *